US012636483B2

(12) United States Patent
Nelson et al.

(10) Patent No.: US 12,636,483 B2
(45) Date of Patent: May 26, 2026

(54) SEALING MEMBER

(71) Applicant: ICU Medical, Inc., San Clemente, CA (US)

(72) Inventors: David Nelson, Long Beach, CA (US); Nicholas Lopez, Laguna Beach, CA (US); Alison D. Burcar, Villa Park, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 16/273,392

(22) Filed: Feb. 12, 2019

(65) Prior Publication Data

US 2020/0009365 A1 Jan. 9, 2020

Related U.S. Application Data

(63) Continuation of application No. 14/131,426, filed as application No. PCT/US2012/044461 on Jun. 27, 2012, now abandoned.

(60) Provisional application No. 61/505,961, filed on Jul. 8, 2011.

(51) Int. Cl.
| | |
|---|---|
| *A61M 39/16* | (2006.01) |
| *A61M 25/00* | (2006.01) |
| *A61M 39/18* | (2006.01) |

(52) U.S. Cl.
CPC .......... *A61M 39/165* (2013.01); *A61M 39/18* (2013.01); *A61M 25/0097* (2013.01); *Y10T 29/49817* (2015.01)

(58) Field of Classification Search
CPC .......... A61M 39/10; A61M 2039/1061; A61M 39/1011; A61M 2039/1027; A61M 39/165; A61M 2039/1033; A61M 39/12; A61M 2039/1083; A61M 2039/1088; A61M 39/26; A61M 2039/1072; F16L 31/00
See application file for complete search history.

(56) References Cited

U.S. PATENT DOCUMENTS

| | | | |
|---|---|---|---|
| 877,946 | A | 2/1908 | Overton |
| 1,793,068 | A | 2/1931 | Dickinson |
| 2,098,340 | A | 11/1937 | Henahan |
| 2,436,297 | A | 2/1948 | Guarnaschelli |
| (Continued) | | | |

FOREIGN PATENT DOCUMENTS

| | | |
|---|---|---|
| CA | 2 148 847 | 12/1995 |
| CA | 2 169 689 | 8/1996 |
| (Continued) | | |

OTHER PUBLICATIONS

Baxter Minicap: Photographs of the Baxter Minicap (Sep. 1, 1998) (4 pages).

(Continued)

*Primary Examiner* — Scott J Medway
(74) *Attorney, Agent, or Firm* — Knobbe, Martens, Olson & Bear, LLP

(57) ABSTRACT

A sheath can be used to protect a catheter hub from contamination. The sheath can surround the catheter hub and seal the interface between the catheter hub and a needleless connector. The sheath can be installed onto the catheter hub either before or after the needleless connector has been connected to the catheter hub.

12 Claims, 2 Drawing Sheets

(56)                    References Cited

U.S. PATENT DOCUMENTS

| | | | | |
|---|---|---|---|---|
| 2,452,643 A | * | 11/1948 | Fields | A61M 39/08 |
| | | | | 206/364 |
| 3,270,743 A | | 9/1966 | Gingras | |
| 3,301,392 A | | 1/1967 | Eddingfield | |
| 3,484,121 A | * | 12/1969 | Quinton | F16L 47/12 |
| | | | | 285/242 |
| 3,882,858 A | | 5/1975 | Klemm | |
| 3,916,929 A | * | 11/1975 | Brown | F16K 17/26 |
| | | | | 137/68.14 |
| 3,977,401 A | | 8/1976 | Pike | |
| 3,987,930 A | | 10/1976 | Fuson | |
| 4,019,512 A | * | 4/1977 | Tenczar | A61M 39/14 |
| | | | | 604/905 |
| 4,022,205 A | * | 5/1977 | Tenczar | F16L 37/30 |
| | | | | 285/21.2 |
| 4,041,934 A | | 8/1977 | Genese | |
| 4,056,116 A | * | 11/1977 | Carter | A61M 39/14 |
| | | | | 251/342 |
| 4,079,738 A | * | 3/1978 | Dunn | A61M 25/0111 |
| | | | | 604/164.05 |
| 4,095,810 A | | 6/1978 | Kulle | |
| 4,149,534 A | * | 4/1979 | Tenczar | A61M 39/14 |
| | | | | 285/125.1 |
| 4,187,846 A | * | 2/1980 | Lolachi | A61M 39/18 |
| | | | | 604/905 |
| 4,192,443 A | | 3/1980 | McLaren | |
| 4,194,509 A | * | 3/1980 | Pickering | A61M 39/1011 |
| | | | | 604/111 |
| 4,230,109 A | * | 10/1980 | Geiss | A61M 39/1011 |
| | | | | D24/129 |
| 4,243,035 A | | 1/1981 | Barrett | |
| 4,256,106 A | * | 3/1981 | Shoor | A61M 39/14 |
| | | | | 604/905 |
| 4,280,632 A | | 7/1981 | Yuhara | |
| 4,294,370 A | | 10/1981 | Toeppen | |
| 4,317,446 A | | 3/1982 | Ambrosio et al. | |
| 4,334,551 A | | 6/1982 | Pfister | |
| 4,335,756 A | | 6/1982 | Sharp et al. | |
| 4,340,052 A | * | 7/1982 | Dennehey | A61M 39/165 |
| | | | | 604/317 |
| 4,384,589 A | | 5/1983 | Morris | |
| 4,402,691 A | | 9/1983 | Rosenthal et al. | |
| 4,405,312 A | | 9/1983 | Gross et al. | |
| 4,417,890 A | | 11/1983 | Dennehey et al. | |
| 4,427,126 A | | 1/1984 | Ostrowsky | |
| 4,432,759 A | | 2/1984 | Gross et al. | |
| 4,432,764 A | | 2/1984 | Lopez | |
| 4,432,766 A | | 2/1984 | Bellotti et al. | |
| 4,439,179 A | | 3/1984 | Lueders et al. | |
| 4,439,184 A | | 3/1984 | Wheeler | |
| 4,440,207 A | | 4/1984 | Genatempo et al. | |
| 4,444,310 A | | 4/1984 | Odell | |
| 4,457,749 A | | 7/1984 | Bellotti et al. | |
| 4,461,368 A | | 7/1984 | Plourde | |
| 4,480,940 A | | 11/1984 | Woodruff | |
| 4,507,111 A | | 3/1985 | Gordon et al. | |
| 4,624,664 A | * | 11/1986 | Peluso | A61M 39/20 |
| | | | | 604/905 |
| 4,631,056 A | * | 12/1986 | Dye | A61M 39/1011 |
| | | | | 604/905 |
| 4,643,711 A | * | 2/1987 | Bates | A61M 5/1582 |
| | | | | 604/177 |
| 4,666,057 A | | 5/1987 | Come et al. | |
| 4,666,427 A | | 5/1987 | Larsson et al. | |
| 4,669,458 A | * | 6/1987 | Abraham | A61M 25/02 |
| | | | | 128/846 |
| 4,671,306 A | | 6/1987 | Spector | |
| 4,673,400 A | * | 6/1987 | Martin | A61M 39/14 |
| | | | | 604/905 |
| 4,703,762 A | | 11/1987 | Rathbone et al. | |
| 4,723,948 A | * | 2/1988 | Clark | A61M 39/12 |
| | | | | 285/243 |
| 4,728,321 A | | 3/1988 | Chen | |
| 4,745,950 A | * | 5/1988 | Mathieu | A61M 39/26 |
| | | | | 604/905 |
| 4,747,502 A | | 5/1988 | Luenser | |
| 4,752,983 A | | 6/1988 | Crieshaber | |
| 4,770,323 A | * | 9/1988 | Debard | B05B 11/02 |
| | | | | 222/89 |
| 4,778,447 A | | 10/1988 | Velde et al. | |
| 4,799,926 A | | 1/1989 | Haber | |
| 4,801,296 A | * | 1/1989 | Vaillancourt | A61M 39/165 |
| | | | | 285/915 |
| 4,810,241 A | | 3/1989 | Rogers | |
| 4,811,847 A | | 3/1989 | Reif et al. | |
| 4,813,933 A | | 3/1989 | Turner | |
| 4,826,486 A | * | 5/1989 | Palsrok | A61M 39/1011 |
| | | | | 128/DIG. 26 |
| 4,834,706 A | * | 5/1989 | Beck | A61M 39/1011 |
| | | | | 604/111 |
| 4,872,471 A | * | 10/1989 | Schneider | F16L 55/1007 |
| | | | | 137/68.14 |
| 4,895,570 A | * | 1/1990 | Larkin | A61M 39/1011 |
| | | | | 604/411 |
| 4,927,019 A | | 5/1990 | Haber et al. | |
| 4,927,423 A | * | 5/1990 | Malmborg | A61J 1/2089 |
| | | | | 604/88 |
| 4,946,455 A | * | 8/1990 | Rosen | F16L 37/367 |
| | | | | 604/905 |
| 4,957,637 A | | 9/1990 | Cornell | |
| 4,983,161 A | | 1/1991 | Dadson et al. | |
| 4,989,733 A | | 2/1991 | Patry | |
| 4,991,629 A | | 2/1991 | Ernesto et al. | |
| 5,037,405 A | * | 8/1991 | Crosby | A61M 39/1011 |
| | | | | 604/533 |
| 5,071,411 A | | 12/1991 | Hillstead | |
| 5,100,394 A | * | 3/1992 | Dudar | A61M 39/14 |
| | | | | 604/537 |
| 5,104,379 A | * | 4/1992 | Nakamura | A61B 1/00062 |
| | | | | 604/111 |
| 5,127,626 A | | 7/1992 | Hilal et al. | |
| 5,143,104 A | | 9/1992 | Iba et al. | |
| 5,176,415 A | * | 1/1993 | Choksi | A61M 39/10 |
| | | | | 128/202.27 |
| 5,190,534 A | | 3/1993 | Kendell | |
| 5,205,821 A | | 4/1993 | Kruger et al. | |
| 5,221,267 A | * | 6/1993 | Folden | A61M 1/28 |
| | | | | 285/4 |
| 5,230,706 A | * | 7/1993 | Duquette | A61M 39/22 |
| | | | | 604/83 |
| 5,242,421 A | | 9/1993 | Chan | |
| 5,242,425 A | * | 9/1993 | White | A61M 39/165 |
| | | | | 604/905 |
| 5,246,011 A | | 9/1993 | Caillouette | |
| D342,134 S | | 12/1993 | Mongeon | |
| 5,352,410 A | | 10/1994 | Hansen et al. | |
| 5,356,396 A | * | 10/1994 | Wyatt | A61M 39/04 |
| | | | | 604/539 |
| 5,360,237 A | * | 11/1994 | Carman | F16L 37/0987 |
| | | | | 24/555 |
| 5,405,336 A | * | 4/1995 | Austin | A61M 25/0014 |
| | | | | 604/534 |
| 5,423,768 A | * | 6/1995 | Folden | A61M 1/28 |
| | | | | 604/200 |
| 5,437,650 A | * | 8/1995 | Larkin | A61M 39/1011 |
| | | | | 604/905 |
| 5,454,409 A | * | 10/1995 | McAffer | A61J 1/18 |
| | | | | 141/329 |
| 5,471,706 A | | 12/1995 | Wallock et al. | |
| 5,507,733 A | | 4/1996 | Larkin et al. | |
| 5,531,695 A | * | 7/1996 | Swisher | A61M 39/1011 |
| | | | | 604/111 |
| 5,536,258 A | | 7/1996 | Folden | |
| 5,552,115 A | | 9/1996 | Malchesky | |
| 5,554,135 A | | 9/1996 | Menyhay | |
| 5,580,530 A | | 12/1996 | Kowatsch et al. | |
| 5,620,088 A | | 4/1997 | Martin et al. | |
| 5,624,402 A | * | 4/1997 | Imbert | A61M 5/3134 |
| | | | | 604/111 |
| 5,694,978 A | | 12/1997 | Heilmann et al. | |

(56)　　　　　References Cited

U.S. PATENT DOCUMENTS

| | | | |
|---|---|---|---|
| 5,702,017 A | 12/1997 | Goncalves | |
| 5,722,537 A | 3/1998 | Sigler | |
| 5,743,892 A | 4/1998 | Loh et al. | |
| 5,762,948 A | 6/1998 | Blackburn et al. | |
| 5,785,691 A * | 7/1998 | Vetter | A61M 5/34 |
| | | | 215/DIG. 3 |
| 5,792,120 A | 8/1998 | Menyhay | |
| 5,810,792 A | 9/1998 | Fangrow, Jr. et al. | |
| 5,820,604 A | 10/1998 | Fox et al. | |
| 5,827,244 A | 10/1998 | Boettger | |
| 5,830,195 A * | 11/1998 | Peters | A61M 39/1011 |
| | | | 604/533 |
| 5,848,994 A * | 12/1998 | Richmond | A61M 5/1411 |
| | | | 604/248 |
| 5,921,419 A * | 7/1999 | Niedospial, Jr. | B65D 51/002 |
| | | | 215/247 |
| 5,941,857 A | 8/1999 | Nguyen et al. | |
| 5,954,957 A | 9/1999 | Chin-Loy et al. | |
| 5,971,972 A | 10/1999 | Rosenbaum | |
| D416,086 S | 11/1999 | Parris et al. | |
| 5,989,229 A | 11/1999 | Chiappetta | |
| 6,045,539 A | 4/2000 | Menyhay | |
| 6,068,148 A * | 5/2000 | Weiler | A61J 1/067 |
| | | | 141/346 |
| 6,083,207 A * | 7/2000 | Heck | A61M 39/06 |
| | | | 604/160 |
| D430,293 S * | 8/2000 | Jansen | D24/129 |
| 6,096,011 A * | 8/2000 | Trombley, III | A61M 39/14 |
| | | | 604/905 |
| 6,099,519 A | 8/2000 | Olsen et al. | |
| 6,113,572 A * | 9/2000 | Gailey | A61M 39/12 |
| | | | 285/12 |
| 6,116,468 A | 9/2000 | Nilson | |
| 6,117,114 A | 9/2000 | Paradis | |
| 6,126,640 A | 10/2000 | Tucker et al. | |
| 6,179,141 B1 | 1/2001 | Nakamura | |
| 6,190,364 B1 | 2/2001 | Imbert | |
| 6,196,998 B1 * | 3/2001 | Jansen | A61M 5/3134 |
| | | | 604/111 |
| 6,202,870 B1 | 3/2001 | Pearce | |
| 6,206,134 B1 | 3/2001 | Stark et al. | |
| 6,217,564 B1 * | 4/2001 | Peters | A61M 39/1011 |
| | | | 604/111 |
| 6,227,391 B1 | 5/2001 | King | |
| 6,245,056 B1 * | 6/2001 | Walker | A61M 39/02 |
| | | | 604/181 |
| 6,250,315 B1 | 6/2001 | Ernster | |
| 6,267,754 B1 | 7/2001 | Peters | |
| 6,270,480 B1 | 8/2001 | Door et al. | |
| 6,315,761 B1 | 11/2001 | Shcherbina et al. | |
| 6,375,231 B1 * | 4/2002 | Picha | A61M 39/1011 |
| | | | 285/114 |
| 6,394,983 B1 | 5/2002 | Mayoral et al. | |
| 6,508,807 B1 | 1/2003 | Peters | |
| 6,550,493 B2 | 4/2003 | Williamson et al. | |
| 6,555,504 B1 | 4/2003 | Ayai et al. | |
| 6,585,691 B1 | 7/2003 | Vitello | |
| 6,595,964 B2 * | 7/2003 | Finley | A61M 39/10 |
| | | | 604/905 |
| 6,666,852 B2 * | 12/2003 | Niedospial, Jr. | A61J 1/2096 |
| | | | 604/88 |
| 6,679,395 B1 | 1/2004 | Pfefferkorn et al. | |
| 6,679,870 B1 | 1/2004 | Finch et al. | |
| 6,685,694 B2 | 2/2004 | Finch et al. | |
| 6,716,396 B1 | 4/2004 | Anderson | |
| 6,722,705 B2 | 4/2004 | Korkor | |
| 6,827,766 B2 | 12/2004 | Carnes et al. | |
| 6,911,025 B2 | 6/2005 | Miyahar | |
| 6,916,051 B2 | 7/2005 | Fisher | |
| 6,943,035 B1 | 9/2005 | Davies et al. | |
| 7,056,308 B2 | 6/2006 | Utterberg | |
| 7,083,605 B2 | 8/2006 | Miyahara | |
| 7,198,611 B2 | 4/2007 | Connell et al. | |
| 7,282,186 B2 | 10/2007 | Lake, Jr. et al. | |
| 7,431,712 B2 | 10/2008 | Kim | |
| 7,452,349 B2 | 11/2008 | Miyahar | |
| 7,516,846 B2 | 4/2009 | Hansen | |
| 7,594,910 B2 * | 9/2009 | Butts | A61M 25/0097 |
| | | | 604/533 |
| 7,618,072 B2 * | 11/2009 | Funamura | A61M 39/1011 |
| | | | 604/533 |
| 7,635,344 B2 | 12/2009 | Tennican et al. | |
| D607,325 S | 1/2010 | Rogers et al. | |
| 7,731,678 B2 | 6/2010 | Tennican et al. | |
| 7,731,679 B2 | 6/2010 | Tennican et al. | |
| 7,749,189 B2 | 7/2010 | Tennican et al. | |
| 7,753,891 B2 | 7/2010 | Tennican et al. | |
| 7,763,006 B2 | 7/2010 | Tennican | |
| 7,766,182 B2 | 8/2010 | Trent et al. | |
| 7,776,011 B2 | 8/2010 | Tennican et al. | |
| 7,780,794 B2 | 8/2010 | Rogers et al. | |
| 7,794,675 B2 | 9/2010 | Lynn | |
| 7,799,010 B2 | 9/2010 | Tennican | |
| 7,857,793 B2 | 12/2010 | Raulerson et al. | |
| 7,922,701 B2 | 4/2011 | Buchman | |
| 7,959,026 B2 | 6/2011 | Bertani | |
| 7,985,302 B2 | 7/2011 | Rogers et al. | |
| 7,993,309 B2 | 8/2011 | Schweikert | |
| 8,047,919 B2 * | 11/2011 | Arden | F16D 9/06 |
| | | | 464/32 |
| 8,065,773 B2 | 11/2011 | Vaillancourt et al. | |
| 8,069,523 B2 | 12/2011 | Vaillancourt et al. | |
| 8,083,728 B2 * | 12/2011 | Rome | A61M 25/0097 |
| | | | 604/533 |
| 8,113,837 B2 | 2/2012 | Zegarelli | |
| 8,162,899 B2 | 4/2012 | Tennican | |
| 8,167,847 B2 | 5/2012 | Anderson et al. | |
| 8,177,066 B2 * | 5/2012 | Tilton | B65D 73/0057 |
| | | | 206/462 |
| 8,206,514 B2 | 6/2012 | Rogers et al. | |
| 8,231,587 B2 | 7/2012 | Solomon et al. | |
| RE43,597 E | 8/2012 | Johnson et al. | |
| 8,235,426 B2 * | 8/2012 | Pisula, Jr. | A61M 39/10 |
| | | | 285/308 |
| 8,252,247 B2 * | 8/2012 | Ferlic | A61M 39/20 |
| | | | 422/309 |
| 8,262,643 B2 | 9/2012 | Tennican | |
| 8,273,303 B2 * | 9/2012 | Ferlic | A61L 2/26 |
| | | | 422/294 |
| 8,328,767 B2 | 12/2012 | Solomon et al. | |
| 8,336,152 B2 | 12/2012 | Kerr et al. | |
| 8,337,475 B2 * | 12/2012 | Christensen | A61M 1/82 |
| | | | 604/317 |
| 8,343,112 B2 | 1/2013 | Solomon et al. | |
| 8,361,408 B2 | 1/2013 | Lynn | |
| 8,372,045 B2 | 2/2013 | Needle et al. | |
| 8,397,756 B2 * | 3/2013 | Packham | F16L 37/32 |
| | | | 137/614.05 |
| 8,419,713 B1 | 4/2013 | Solomon et al. | |
| 8,480,968 B2 | 7/2013 | Lynn | |
| 8,523,830 B2 | 9/2013 | Solomon et al. | |
| 8,523,831 B2 | 9/2013 | Solomon et al. | |
| 8,545,479 B2 | 10/2013 | Kitani et al. | |
| 8,603,022 B2 * | 12/2013 | Lyons | A61M 1/3659 |
| | | | 604/6.16 |
| 8,641,681 B2 | 2/2014 | Solomon et al. | |
| 8,647,308 B2 | 2/2014 | Solomon et al. | |
| 8,647,326 B2 | 2/2014 | Solomon et al. | |
| 8,671,496 B2 | 3/2014 | Kerr et al. | |
| 8,684,979 B2 * | 4/2014 | Deighan | A61M 39/1011 |
| | | | 285/332.1 |
| 8,740,864 B2 | 6/2014 | Hoang et al. | |
| 8,777,504 B2 | 7/2014 | Shaw et al. | |
| 8,845,593 B2 | 9/2014 | Anderson et al. | |
| 8,864,707 B1 * | 10/2014 | Vitello | A61M 39/20 |
| | | | 604/111 |
| 8,968,268 B2 | 3/2015 | Anderson et al. | |
| 9,072,296 B2 | 7/2015 | Mills et al. | |
| 9,078,992 B2 | 7/2015 | Ziebol et al. | |
| 9,095,500 B2 | 8/2015 | Brandenburger et al. | |
| 9,095,667 B2 | 8/2015 | Von Schuckmann | |
| 9,097,370 B2 | 8/2015 | Schnell et al. | |

(56) References Cited

U.S. PATENT DOCUMENTS

| | | | |
|---|---|---|---|
| 9,101,750 B2 | 8/2015 | Solomon et al. | |
| 9,114,915 B2 | 8/2015 | Solomon et al. | |
| 9,125,600 B2 | 9/2015 | Steube et al. | |
| 9,149,624 B2 | 10/2015 | Lewis | |
| 9,180,252 B2 | 11/2015 | Gelblum et al. | |
| 9,192,449 B2 | 11/2015 | Kerr et al. | |
| 9,216,440 B2 | 12/2015 | Ma et al. | |
| 9,233,208 B2 | 1/2016 | Tekeste | |
| 9,242,084 B2 | 1/2016 | Solomon et al. | |
| 9,259,284 B2 | 2/2016 | Rogers et al. | |
| 9,259,535 B2 | 2/2016 | Anderson et al. | |
| 9,283,367 B2 | 3/2016 | Hoang et al. | |
| 9,283,368 B2 | 3/2016 | Hoang et al. | |
| 9,283,369 B2 | 3/2016 | Ma et al. | |
| 9,289,588 B2 | 3/2016 | Chen | |
| 9,302,049 B2 | 4/2016 | Tekeste | |
| 9,345,641 B2 | 5/2016 | Krause et al. | |
| 9,352,140 B2 | 5/2016 | Kerr et al. | |
| 9,352,141 B2 | 5/2016 | Wong | |
| 9,399,125 B2 | 7/2016 | Burkholz | |
| 9,408,971 B2 | 8/2016 | Carlyon | |
| 9,527,660 B2 | 12/2016 | Tennican | |
| 9,592,375 B2 | 3/2017 | Tennican | |
| 9,700,676 B2 | 7/2017 | Anderson et al. | |
| 9,700,677 B2 | 7/2017 | Anderson et al. | |
| 9,700,710 B2 | 7/2017 | Anderson et al. | |
| 9,707,308 B2 * | 7/2017 | Ferlic | A61L 2/235 |
| 9,707,348 B2 | 7/2017 | Anderson et al. | |
| 9,707,349 B2 | 7/2017 | Anderson et al. | |
| 9,707,350 B2 | 7/2017 | Anderson et al. | |
| 10,357,643 B2 * | 7/2019 | Buchanan | A61M 39/105 |
| 10,857,346 B2 * | 12/2020 | Dennis | A61M 39/1011 |
| 2002/0129858 A1 * | 9/2002 | Meyer | F16K 15/18 |
| | | | 137/625.48 |
| 2002/0193752 A1 | 12/2002 | Lynn | |
| 2003/0060749 A1 | 3/2003 | Aneas | |
| 2003/0153865 A1 | 8/2003 | Connell et al. | |
| 2003/0201639 A1 * | 10/2003 | Korkor | F16L 19/0237 |
| | | | 285/81 |
| 2004/0034042 A1 | 2/2004 | Tsuji et al. | |
| 2004/0048542 A1 | 3/2004 | Thomascheisky et al. | |
| 2004/0092890 A1 | 5/2004 | Ash | |
| 2004/0199143 A1 * | 10/2004 | Lauer | A61M 39/14 |
| | | | 604/533 |
| 2004/0215148 A1 | 10/2004 | Hwang et al. | |
| 2004/0238776 A1 * | 12/2004 | Peters | A61M 39/1011 |
| | | | 604/905 |
| 2005/0013836 A1 | 1/2005 | Raad | |
| 2005/0065479 A1 | 3/2005 | Schiller et al. | |
| 2005/0074485 A1 | 4/2005 | Lipton | |
| 2005/0124970 A1 | 6/2005 | Kunin et al. | |
| 2005/0147524 A1 | 7/2005 | Bousquet | |
| 2005/0148930 A1 | 7/2005 | Hseih et al. | |
| 2005/0214185 A1 | 9/2005 | Castaneda | |
| 2005/0281832 A1 | 12/2005 | Campbell | |
| 2006/0064159 A1 * | 3/2006 | Porter | A61M 1/3661 |
| | | | 623/1.24 |
| 2006/0142735 A1 * | 6/2006 | Whitley | A61M 39/26 |
| | | | 604/537 |
| 2007/0167910 A1 | 7/2007 | Tennican et al. | |
| 2007/0187353 A1 | 8/2007 | Fox et al. | |
| 2007/0202177 A1 | 8/2007 | Hoang | |
| 2007/0249996 A1 | 10/2007 | Tennican et al. | |
| 2007/0265578 A1 | 11/2007 | Tennican et al. | |
| 2007/0287989 A1 | 12/2007 | Crawford et al. | |
| 2008/0027399 A1 | 1/2008 | Harding et al. | |
| 2008/0033371 A1 | 2/2008 | Updegraff et al. | |
| 2008/0039803 A1 | 2/2008 | Lynn | |
| 2008/0058733 A1 | 3/2008 | Vogt et al. | |
| 2008/0093245 A1 | 4/2008 | Periasamy et al. | |
| 2008/0095680 A1 | 4/2008 | Steffens et al. | |
| 2008/0147047 A1 | 6/2008 | Davis et al. | |
| 2008/0177250 A1 | 7/2008 | Howlett et al. | |

| | | | |
|---|---|---|---|
| 2009/0001718 A1 * | 1/2009 | Vinci | A61M 1/1668 |
| | | | 285/307 |
| 2009/0008393 A1 | 1/2009 | Howlett et al. | |
| 2009/0012426 A1 | 1/2009 | Tennican | |
| 2009/0062766 A1 | 3/2009 | Howlett et al. | |
| 2009/0093757 A1 | 4/2009 | Tennican | |
| 2009/0099529 A1 | 4/2009 | Anderson et al. | |
| 2009/0137969 A1 | 5/2009 | Colantonio et al. | |
| 2009/0187158 A1 * | 7/2009 | Richmond | A61M 39/221 |
| | | | 604/414 |
| 2009/0192463 A1 * | 7/2009 | Nardeo | A61M 25/0668 |
| | | | 604/164.01 |
| 2009/0205151 A1 | 8/2009 | Fisher et al. | |
| 2009/0205656 A1 | 8/2009 | Nishibayashi et al. | |
| 2009/0259194 A1 | 10/2009 | Pinedjian et al. | |
| 2010/0003067 A1 | 1/2010 | Shaw et al. | |
| 2010/0022956 A1 * | 1/2010 | Tipsmark | A61M 25/02 |
| | | | 604/154 |
| 2010/0047123 A1 | 2/2010 | Solomon et al. | |
| 2010/0049170 A1 | 2/2010 | Solomon et al. | |
| 2010/0050351 A1 | 3/2010 | Colantonio et al. | |
| 2010/0064456 A1 | 3/2010 | Ferlic | |
| 2010/0152670 A1 | 6/2010 | Low | |
| 2010/0160894 A1 | 6/2010 | Julian et al. | |
| 2010/0172794 A1 | 7/2010 | Ferlic et al. | |
| 2010/0191219 A1 | 7/2010 | Gupta et al. | |
| 2010/0242993 A1 | 9/2010 | Hoang et al. | |
| 2010/0306938 A1 | 12/2010 | Rogers et al. | |
| 2010/0331822 A1 * | 12/2010 | Willemstyn | A61M 39/1011 |
| | | | 604/533 |
| 2011/0030726 A1 | 2/2011 | Vaillancourt et al. | |
| 2011/0044850 A1 | 2/2011 | Solomon et al. | |
| 2011/0046564 A1 | 2/2011 | Zhong | |
| 2011/0046603 A1 | 2/2011 | Felsovalyi et al. | |
| 2011/0064512 A1 | 3/2011 | Shaw et al. | |
| 2011/0082431 A1 * | 4/2011 | Burgess | A61M 39/1011 |
| | | | 604/240 |
| 2011/0086101 A1 | 4/2011 | Madhyastha et al. | |
| 2011/0217212 A1 | 9/2011 | Solomon et al. | |
| 2011/0232020 A1 | 9/2011 | Rogers et al. | |
| 2011/0265825 A1 | 11/2011 | Rogers et al. | |
| 2011/0311602 A1 | 12/2011 | Mills et al. | |
| 2012/0031904 A1 | 2/2012 | Kuhn et al. | |
| 2012/0039764 A1 | 2/2012 | Solomon et al. | |
| 2012/0109073 A1 | 5/2012 | Anderson et al. | |
| 2012/0157965 A1 | 6/2012 | Wotton et al. | |
| 2012/0191067 A1 | 7/2012 | Chia et al. | |
| 2012/0195807 A1 | 8/2012 | Ferlic | |
| 2012/0216359 A1 | 8/2012 | Rogers et al. | |
| 2012/0216360 A1 | 8/2012 | Rogers et al. | |
| 2012/0283696 A1 | 11/2012 | Cronenberg et al. | |
| 2012/0289591 A1 | 11/2012 | Folan | |
| 2012/0296284 A1 | 11/2012 | Anderson et al. | |
| 2012/0302970 A1 | 11/2012 | Tennican | |
| 2012/0302997 A1 | 11/2012 | Gardner et al. | |
| 2013/0030414 A1 | 1/2013 | Gardner et al. | |
| 2013/0035667 A1 | 2/2013 | Anderson et al. | |
| 2013/0053751 A1 | 2/2013 | Holtham | |
| 2013/0072908 A1 | 3/2013 | Solomon et al. | |
| 2013/0098398 A1 | 4/2013 | Kerr et al. | |
| 2013/0123754 A1 | 5/2013 | Solomon et al. | |
| 2013/0171030 A1 | 7/2013 | Ferlic et al. | |
| 2013/0178526 A1 | 7/2013 | Ash et al. | |
| 2013/0183635 A1 | 7/2013 | Wilhoit | |
| 2013/0197485 A1 | 8/2013 | Gardner et al. | |
| 2013/0231302 A1 | 9/2013 | Raad et al. | |
| 2013/0237946 A1 * | 9/2013 | Lynn | A61J 1/1487 |
| | | | 604/414 |
| 2013/0274686 A1 | 10/2013 | Ziebol et al. | |
| 2014/0048079 A1 | 2/2014 | Gardner et al. | |
| 2014/0052074 A1 | 2/2014 | Tekeste | |
| 2014/0101876 A1 | 4/2014 | Rogers et al. | |
| 2014/0155868 A1 | 6/2014 | Nelson et al. | |
| 2014/0228809 A1 | 8/2014 | Wong | |
| 2014/0339812 A1 | 11/2014 | Carney et al. | |
| 2014/0339813 A1 | 11/2014 | Cederschiöld et al. | |
| 2015/0018774 A1 | 1/2015 | Anderson et al. | |
| 2015/0141934 A1 | 5/2015 | Gardner et al. | |
| 2015/0148287 A1 | 5/2015 | Woo et al. | |

(56) References Cited

U.S. PATENT DOCUMENTS

| | | | |
|---|---|---|---|
| 2015/0165127 A1 | 6/2015 | Haefele et al. | |
| 2015/0217106 A1 | 8/2015 | Banik et al. | |
| 2015/0231380 A1 | 8/2015 | Hoang et al. | |
| 2015/0237854 A1 | 8/2015 | Mills et al. | |
| 2015/0238703 A1 | 8/2015 | Glocker | |
| 2015/0273199 A1 | 10/2015 | Adams et al. | |
| 2015/0297455 A1 | 10/2015 | Sanders et al. | |
| 2015/0297881 A1 | 10/2015 | Sanders et al. | |
| 2015/0306369 A1 | 10/2015 | Burkholz et al. | |
| 2015/0314119 A1 | 11/2015 | Anderson et al. | |
| 2015/0314120 A1 | 11/2015 | Gardner et al. | |
| 2015/0320926 A1 | 11/2015 | Fitzpatrick et al. | |
| 2015/0374968 A1 | 12/2015 | Solomon et al. | |
| 2016/0001058 A1 | 1/2016 | Ziebol et al. | |
| 2016/0015931 A1 | 1/2016 | Ryan et al. | |
| 2016/0015959 A1 | 1/2016 | Solomon et al. | |
| 2016/0045629 A1 | 2/2016 | Gardner et al. | |
| 2016/0067365 A1 | 3/2016 | Ma et al. | |
| 2016/0067471 A1 | 3/2016 | Ingram et al. | |
| 2016/0088995 A1 | 3/2016 | Ueda et al. | |
| 2016/0089530 A1 | 3/2016 | Sathe | |
| 2016/0101276 A1 | 4/2016 | Tekeste | |
| 2016/0106969 A1 | 4/2016 | Neftel | |
| 2016/0121097 A1 | 5/2016 | Steele | |
| 2016/0144118 A1 | 5/2016 | Solomon et al. | |
| 2016/0158520 A1 | 6/2016 | Ma et al. | |
| 2016/0158521 A1 | 6/2016 | Hoang et al. | |
| 2016/0158522 A1 | 6/2016 | Hoang et al. | |
| 2016/0184527 A1 | 6/2016 | Tekeste | |
| 2016/0213912 A1 | 7/2016 | Daneluzzi | |
| 2016/0250420 A1 | 9/2016 | Maritan et al. | |
| 2017/0361023 A1 | 12/2017 | Anderson et al. | |
| 2018/0058618 A1* | 3/2018 | Walterspiel | A61M 16/0875 |

FOREIGN PATENT DOCUMENTS

| | | | |
|---|---|---|---|
| CN | 2402327 Y | 10/2000 | |
| CN | 2815392 Y | 9/2006 | |
| CN | 201150420 Y | 11/2008 | |
| CN | 201519335 U | 7/2010 | |
| DE | 89 06 628 U1 | 9/1989 | |
| DE | 29617133 | 1/1997 | |
| EP | 0 108 785 | 5/1984 | |
| EP | 0 227 219 | 7/1987 | |
| EP | 0 245 872 | 11/1987 | |
| EP | 0 769 265 | 4/1997 | |
| EP | 1 061 000 | 10/2000 | |
| EP | 1 331 020 | 7/2003 | |
| EP | 1 977 714 | 10/2008 | |
| EP | 2 444 117 | 4/2012 | |
| FR | 2 493 149 A | 5/1982 | |
| FR | 2 782 910 | 3/2000 | |
| GB | 123221 | 2/1919 | |
| GB | 2 296 182 | 6/1996 | |
| GB | 2 333 097 | 7/1999 | |
| GB | 2 387 772 | 10/2003 | |
| JP | 04-99950 | 2/1992 | |
| JP | 2002-291906 | 10/2002 | |
| JP | 2006-182663 A | 7/2006 | |
| RU | 2 246 321 C1 | 2/2005 | |

| | | | |
|---|---|---|---|
| WO | WO 1983/03975 | 11/1983 | |
| WO | WO 1985/05040 | 11/1985 | |
| WO | WO 1998/12125 | 3/1998 | |
| WO | WO 1998/048694 | 11/1998 | |
| WO | WO 2000/01391 | 1/2000 | |
| WO | WO 2004/035129 | 4/2004 | |
| WO | WO 2004/112846 | 12/2004 | |
| WO | WO 2006/007690 | 1/2006 | |
| WO | WO 2006/044236 | 4/2006 | |
| WO | WO 2007/056773 | 5/2007 | |
| WO | WO 2007/137056 | 11/2007 | |
| WO | WO 2008/086631 | 7/2008 | |
| WO | WO 2008/089196 | 7/2008 | |
| WO | WO 2008/100950 | 8/2008 | |
| WO | WO 2008/140807 | 11/2008 | |
| WO | WO 2009/002474 | 12/2008 | |
| WO | WO 2009/117135 | 9/2009 | |
| WO | WO 2009/123709 | 10/2009 | |
| WO | WO 2009/136957 | 11/2009 | |
| WO | WO 2009/153224 | 12/2009 | |
| WO | WO 2010/002757 | 1/2010 | |
| WO | WO 2010/002808 | 1/2010 | |
| WO | WO 2010/039171 | 4/2010 | |
| WO | WO 2011/028722 | 3/2011 | |
| WO | WO 2011/119021 | 9/2011 | |
| WO | WO 2012/162006 | 11/2012 | |
| WO | WO 2013/009478 A1 | 1/2013 | |
| WO | WO 2013/192574 | 12/2013 | |

OTHER PUBLICATIONS

Baxter, "Peritoneal Dialysis Patient Connectology," Product Descriptions in 1 page, downloaded Jul. 1, 2011.

Catheter Connections, "Disinfectant Caps for Luer Access Valves and Male Luer Connectors," Instructions for Use in 1 page [Publication Date unknown] Per Albert—no longer use—Do Not Submit.

Catheter Connections, "Introducing DualCap," Product Brochure in 1 page, Copyright 2011.

Conical Fittings: International Standard, "Conical fittings with 6% (Luer) Taper for Syringes, Needles and certain Other Medical Equipment—Part 2: Lock Fittings", Ref. No. ISO 594-2:1998. International Organization for Standardization (Sep. 1, 1998) 2nd ed. (16 pages).

Devine, redacted version of letter from David A. Divine, Esq. of Lee & Hayes, dated May 16, 2011 (3 pages).

Devine, redacted version of letter from David A. Divine, Esq. of Lee & Hayes, dated May 27, 2011 (3 pages).

European Search Report re EP Application No. 15746744.0, dated Jul. 10, 2017).

Hospira, "You Work in Neverland," Lifeshield Product Brochure in 2 pages [Product appears to have been released in 2009] Do not submit in the 002A/C2 families.

Hyprotek, "Port Protek," Product Brochure in 1 page, downloaded Sep. 19, 2011 from http://www.hyprotek.com/products.html.

Menyhay et al., "Disinfection of Needleless Catheter Connectors and Access Ports with Alcohol May Not Prevent Microbial Entry: The Promise of a Novel Antiseptic-Barrier Cap" Infection Control Hospital and Epidemiology, vol. 27, No. 1 (Jan. 2006) (5 pages).

Photographs of the Baxter Minicap (Sep. 1, 1998) (4 pages).

* cited by examiner

SEALING MEMBER

CROSS-REFERENCE TO RELATED APPLICATIONS

This application is a continuation of U.S. patent application Ser. No. 14/131,426, filed Jan. 7, 2014, titled "SHEATH," which claims the benefit under 35 U.S.C. § 120 and 35 U.S.C. § 365(c) as a national phase application of International Application No. PCT/US2012/044461, designating the United States, with an international filing date of Jun. 27, 2012, titled "SHEATH," which claims priority to U.S. Provisional Application No. 61/505,961 filed Jul. 8, 2011, titled "SHEATH." The entire contents of the above are incorporated by reference herein.

BACKGROUND OF THE DISCLOSURE

Field of the Disclosure

Embodiments relate generally to medical catheter systems through which fluids flow, and in particular, to sheaths or covers related to catheter hubs and needleless medical connectors.

Description of the Related Art

Catheter systems of connectors, valves, and tubing are routinely used in hospitals and other medical settings to facilitate the transfer of fluids to and from patients. Efforts are routinely made to follow aseptic practice to combat contamination.

SUMMARY OF SOME EMBODIMENTS

A sheath can be used to seal and/or cover various parts of a catheter system to prevent contamination from entering the catheter system. A sheath as will be described herein can be used to reduce the chance of infection.

A sheath can comprise a flexible housing configured to sealingly engage medical tubing at one end and to sealingly engage and cover a connection between a catheter hub and a needleless connector.

According to some embodiments, a sheath can have a flexible housing. The flexible housing can comprise a first end configured to cover and create a fluid tight seal around a connection between a catheter hub and a needleless connector and a second end spaced from the first end such that the housing completely encloses the catheter hub. The flexible housing can be configured for initial attachment to the catheter hub independent of whether the needleless connector is already connected to the catheter hub and can be configured to tear so as to facilitate removal.

In some embodiments, the flexible housing can be configured to be removed by destruction such as being configured to preferably tear along the sides in two locations generally parallel with one another or to break into two pieces, rendering the device unusable thereafter.

BRIEF DESCRIPTION OF THE DRAWINGS

These and other features, aspects, and advantages are described below with reference to the drawings, which are intended to illustrate but not to limit embodiments of the invention. In the drawings, like reference characters denote corresponding features consistently throughout similar embodiments.

DETAILED DESCRIPTION OF THE PREFERRED EMBODIMENT

A sheath 10 can be used to seal, cover, and/or protect various parts of a catheter system. The sheath 10 can beneficially be used to reduce contamination or bacteria from entering the blood stream of a patient. In some embodiments, the sheath 10 can be disposable and can be an easily replaceable part of a catheter system. In this way, the sheath 10 can be a sacrificial first line of defense for the catheter system. When the sheath 10 is removed, it preferably takes any contaminates from the site along with it. This can prevent direct contact with, and contamination of, sensitive and/or important areas of a catheter system of connectors, valves, and tubing. The site can then be better prepared for any necessary additional action such as, for example, connecting or disconnecting connectors, valves, and tubing.

The connection or access portions of the catheter system can be considered the weak points or danger points where there is significant risk of spreading disease to the patient. The connection locations and access sites generally allow direct contact or access to the blood stream. This can occur, if for example, the connection is loosened, or changed, a connection is made, or components are replaced. If proper procedures are not taken, bacteria can enter the blood stream causing infection. Even when proper procedures are taken, there is still a risk of infection.

A sheath 10 can be used to reduce the risk of infection. Some embodiments of a sheath 10 can protect an access site and then be removed, thereby removing contaminates from the site. The newly exposed section of the catheter system can be handled in a sterile manner for whatever actions are desired and then a new sheath can be added to the system. The sheath acts as a barrier to prevent the underlying areas from contacting potentially harmful or contaminating substances, surfaces, and/or objects.

Figures 1, 2:
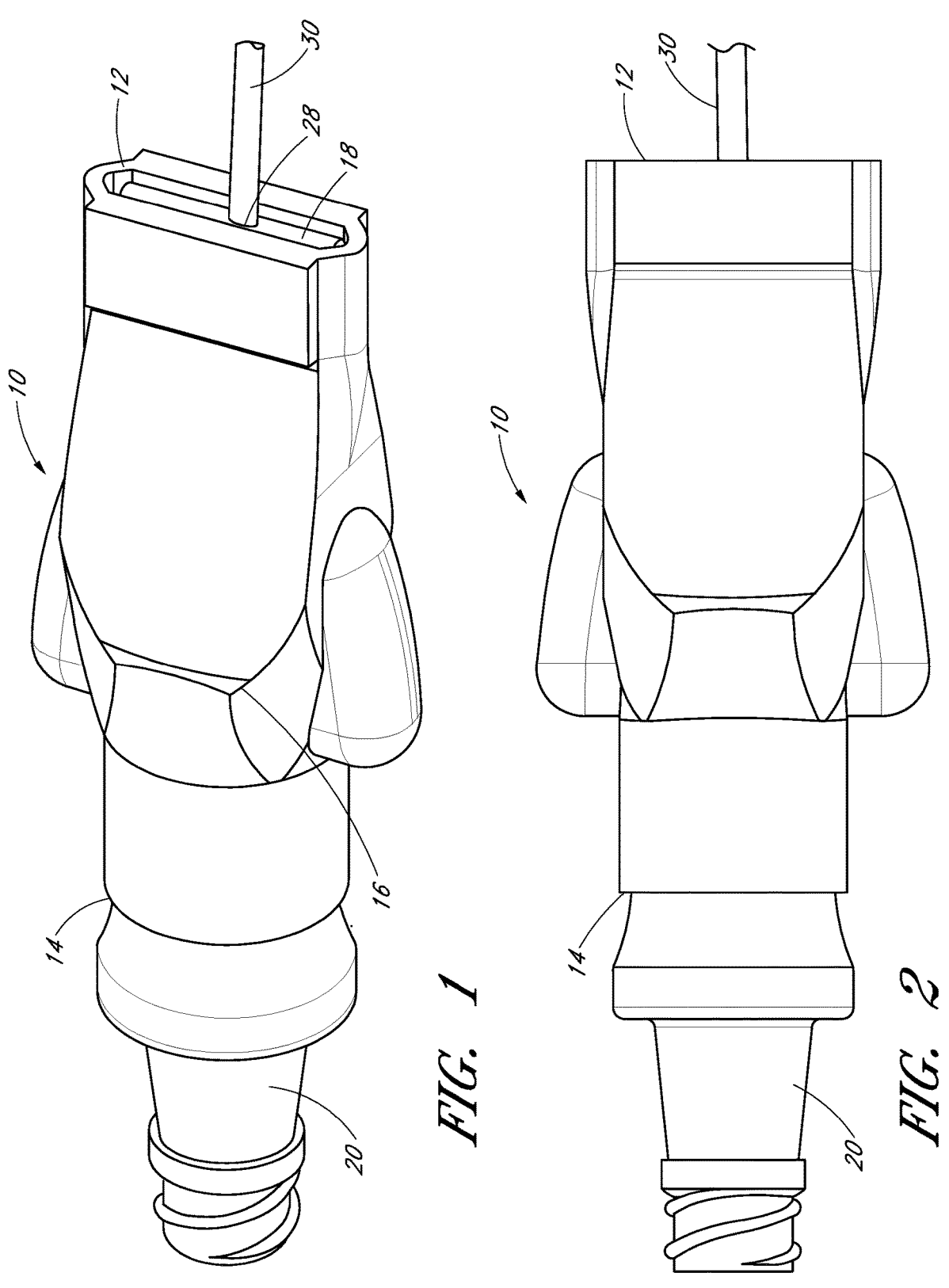
FIGS. 1 and 2 illustrate an embodiment of a sheath coupled to a catheter hub and a needleless connector.
Figure 3:
FIG. 3 shows a cross-section of the system shown in FIG. 2.

FIGS. 1-3 illustrate part of a catheter system where a sheath 10 is used to cover a catheter hub 40 (FIG. 3) and the connection between the catheter hub 40 and a needleless or needle-free connector 20. The catheter hub 40 can be connected to tubing 30.

The sheath 10 can protect the catheter hub 40 from contacting potentially contaminated surfaces. The sheath 10 can be used to establish a barrier between a section of the catheter system and its surroundings.

The catheter system can be used for many purposes, such as intravenous infusion and/or withdrawal of fluids. For example, the catheter hub 40 and tubing 30 could be part of a peripherally inserted central catheter (PICC or PIC line). A PICC is inserted in a peripheral vein, such as the cephalic vein, basilic vein, or brachial vein and then advanced through increasingly larger veins, toward the heart until the tip rests in the distal superior vena cava or cavoatrial junction.

A PICC is generally placed in a patient for a long term treatment such as for long chemotherapy regimens, extended antibiotic therapy, or total parenteral nutrition. As has been mentioned, long term treatment increases the risk of infection. Thus, a sheath 10 can be used to decrease this risk.

Looking to FIGS. 1 and 2, it can be seen that the sheath 10 can completely enclose the catheter hub 40, such that the catheter hub cannot be seen or touched. In some embodiments, a clear or substantially transparent sleeve may be used which would facilitate assembly of the system. The catheter hub is connected to tubing 30 that protrudes out one end 12 of the sheath, while a needleless connector 20 connected to the other end of the catheter hub, protrudes out the other end 14 of the sheath 10. As shown, the needleless connector 20 is a version of the CLAVE® needleless connector with the male luer end 22 connected to the catheter hub 40 (FIG. 3). The needleless connector 20 also has a valved female luer end 24. One of many different types of needleless connectors can be used to connect to the catheter hub 40. In addition, the catheter hub could be one of many different types of catheter hubs.

The needleless connector 20 can be used to gain access into the catheter system, such as to inject medicaments or to withdraw blood. In typical use, a needleless connector 20 provides a sealed interface 24 that can be sterilized, such as with an antiseptic wipe, prior to connecting another device with the needleless connector, thereby opening the sealed interface and moving the valve 26 (FIG. 3).

As has been mentioned, the needleless connector 20 can attach to one end of the catheter hub 40. The sheath 10 can be used to seal the interface 32 between the catheter hub 40 and the needleless connector 20. The sheath can also enclose and surround the catheter hub 40. In this way, the sheath 10 can keep the catheter hub 40 and the interface 32 between the catheter hub 40 and the needleless connector 20 clean and generally free of debris.

As will be understood, the catheter hub 40 is connected to tubing 30 as part of a catheter system that may be implanted within a patient for an extended period of time. This period of time may be days, weeks, months, etc. As such, it may be generally desired that the catheter hub 40 remain in place and not be removed. As the catheter hub 40 is attached to the tubing 30 it can be difficult to remove the catheter hub without also replacing the tubing. It may be undesirable to replace the tubing for many reasons as will be known by those of skill in the art. In contrast, the needleless connector 20 can be easily removed and replaced.

Similarly, in some embodiments, the sheath 10 can also be easily removed and replaced. Thus, the sheath 10 can provide a flexible disposable barrier that surrounds the catheter hub 40. As the catheter hub 40 may remain in place as part of a catheter system in a patient for an extended period of time, the sheath 10 can beneficially protect the catheter hub from undesired contamination. The sheath 10 can also be removed after a certain time period taking any contaminates with it. The sheath 10 can then be replaced by a new sterile sheath 10. In some embodiments, the sheath 10 may be integrally formed with, or permanently connected to, connector 20 such that the sheath 10 is removed with the connector 20. The connector/sheath combination can then be replaced with a new connector/sheath combination or can be replaced with a connector and a separate sheath.

The installation and removal of the sheath will now be described.

The sheath 10 can be configured to fit over most catheter hubs and needleless connectors. This can be a result of many reasons including material selection and certain design features. For example, the sheath can have a flexible outer housing. In some embodiments, the outer housing can be elastomeric, or a portion can be elastomeric. The elastomeric portion can be stretched as the sheath 10 is passed over the catheter hub and/or needleless connector.

The sheath 10 can slip over the catheter hub 40 either before or after a needleless connector 20 has been connected to the catheter hub 40. As the sheath 10 can have a flexible outer housing, the sheath 10 can be forced to pass over the catheter hub 40 and/or needleless connector 20. The outer housing can expand and move in a flexible manner as needed to reach the desired position.

In some embodiments, the sheath can be actuated or otherwise acted upon to open an end 12 of the sheath 10. For example, the end 12 or a middle section 16 can be pinched by a user's fingers to cause the end 12 to open to allow the catheter hub 40 and/or needleless connector 20 to pass through the sheath 10.

The end 12 of the sheath 10 can be configured to close or to substantially close around the tubing 30. In some embodiments, the end 12 includes a closure system 18. The closure system 18 can be a tongue and groove system where the tongue is configured to fit within the groove when the sheath is attached to the catheter hub 40. The closure system can also include sidewalls that are forced into contact one with the other. Other configurations are also possible.

The end 12 of the sheath can also include a passageway 28 that passes through the end 12. The passageway 28 can be permanent or temporary or can only open in certain positions of the sheath 10, such as when the sheath is installed on the catheter hub 40. The passageway can be configured such that the tubing 30 passes through the passageway 28. In some configurations, the tubing and passageway 28 and/or end 12 can form a first peripheral seal 50 such that the sheath 10 sealingly engages the sidewalls of the tubing 30, while still allowing the tubing to pass through the end 12. The seal 50 can be a water-tight or a near water-tight seal.

The end 14 of the sheath can be sized to accept the needleless connector 20 and form a second peripheral seal 52 along the sides of the needleless connector 20. In some embodiments the second seal 52 can be formed at or near the connector end 22. Alternatively it may be positioned at other locations along the connector 20. The sheath 10 can also seal the interface 32 between the catheter hub 40 and the needleless connector 20. An internal seal 54 can also be formed in some configurations between a radially extending portion 42 of the catheter hub 40 and the end 22 of the needleless connector 20. As shown, the end 22 of the needleless connector 20 includes internal male luer threads and an end surface 22a. In some embodiments the sheath 10 can be positioned between the end surface 22a and the radially extending portion 42 to create a washer-like seal. Whether the seal 54 is formed can depend on the particular size and configuration of the catheter hub and needleless connector chosen.

The seals 50, 52, 54 around the catheter hub and the needleless connector can be water-tight or near water-tight. Where a portion of the sheath is elastomeric, stretching of the elastomeric material can be used to create a seal between the sheath 10 and one or more of the catheter hub 40, the needleless connector 20, and/or the tubing 30.

In some embodiments, the needleless connector 20 can be attached to the catheter hub 40 either before or after the sheath 10 has been attached to the catheter hub 40. Thus, the needleless connector can be removed and/or replaced without removing the sheath 10. In addition, the sheath 10 can maintain the catheter hub 40 and a portion of the tubing in an enclosed, protected and sealed state independent of the placement of the needleless connector.

In alternative embodiments, the sheath 10 can be made integrally with the needleless connector 20. In this configuration removing the needleless connector would also remove the sheath.

Returning to FIG. 3, it can be seen that in some embodiments the sheath 10 has an internal chamber 34. The internal chamber 34 can enclose a portion of the tubing 30 as well as the catheter hub 40. The sheath end 12 can be spaced away from the catheter hub 40 to also enclose a section of the tubing 36 adjacent the catheter hub 40. This can provide additional protection such that when the sheath is removed there is a decreased risk of contamination getting into or on the catheter hub. Thus, there is also a corresponding decreased risk of infection. In some embodiments, the chamber 34 can include a disinfectant, antibacterial, or antimicrobial solution or other material to increase the effectiveness of the barrier. In some embodiments, the sheath 10 itself may include or exude a disinfectant, antimicrobial, or antibacterial material.

The length of tubing 36 adjacent the catheter hub 40 that is enclosed within the sheath 10 can be as long, longer or shorter than the catheter hub itself.

In some embodiments, the sheath 10 can be configured to be non-reusable and/or removed by destruction. Removal by destruction can prevent a used and contaminated sheath 10 from being reused. For example, the sheath 10 can be configured to break or tear along a release portion 38. The sheath 10 can utilize one or more seams, thin walled sections, tear away sections, etc., or combinations thereof to create the release portion 38. The release portion 38 can be used to cause the sheath 10 to separate from the other components of the catheter system. For example, portions of the sheath 10 can be pulled in opposite directions causing the release portion 38 to break or tear and the sheath 10 to split apart. The release portion 38 can extend along a portion of or the entire sheath 10.

In some typical uses of a catheter system, the needleless connector 20 is often removed from the catheter hub 40 and replaced with a new needleless connector after a period of time, for example 3 days. A sheath can beneficially be added to such a system. The sheath 10 can also be removed and replaced at the same time as the needleless connector 20. For example, the sheath 10 can be ripped off the catheter hub, utilizing the release portion 38. The needleless connector can then be removed. Afterwards, a new sheath can be connected to the catheter hub, followed by a new needleless connector. In this manner contaminants can be removed from the site with the removal of the sheath before the needleless connector is removed which opens the injection site to exposure to air and potential contaminant.

The sheath 10 can provide many benefits. For example, the sheath can cover all or part of a section of a catheter system. This can allow the section to remain protected from contacting potentially harmful or contaminated surfaces or objects. Also, the sheath can be removed and replaced with a new sterile sheath. This removes any contaminates at the site and can further reduce the risk of infection.

Embodiments of the sheath can be added at one of many different times in the assembly procedure, such before or after the needleless connector has been connected to the catheter hub. Some embodiments of the sheath also seal the catheter hub at one end while enclosing some or the entire catheter hub and can form a seal with the body of the catheter hub while still allowing for connection to or disconnection from a needleless connector, thereby providing a protected catheter hub.

Some embodiments of the sheath can be non-reusable and disposable. Embodiments can be removed by destruction to prevent the sheath from being reused and potentially contaminating the catheter hub. Embodiments can have tear away portions and can be removable and separable from all other pieces.

Although this invention has been disclosed in the context of certain embodiments and examples, it will be understood by those skilled in the art that the invention extends beyond the disclosed embodiments to other alternative embodiments and/or uses of the invention and obvious modifications and equivalents thereof. Additionally, it is contemplated that various aspects and features of embodiments of the invention described can be practiced separately, combined together, or substituted for one another, and that a variety of combination and sub-combinations of the features and aspects can be made and still fall within the scope of the invention. Thus, it is intended that the scope of the invention should not be limited by the above description, but should be determined only by the claims.

What is claimed is:

1. A method of establishing a medical fluid connection in an intravenous infusion catheter system between a first medical connector and a second medical connector with enhanced contamination prevention, the method comprising:

providing a first medical connector comprising a male luer end having a male luer and a shroud surrounding at least a portion of the male luer, providing a second medical connector comprising a complimentary end being configured to fluidly connect to the male luer end of the first medical connector, providing an elastomeric sealing member being configured to engage with an outer surface of the shroud of the first medical connector to form a first seal between the elastomeric sealing member and the shroud, the elastomeric sealing member including a middle section with opposing side portions extending wider than the shroud of the first medical connector, the middle section configured to be pinched to open an end of the elastomeric sealing member to facilitate passage of the second medical connector; and connecting the complimentary end of the second medical connector to the male luer end of the first medical connector to establish fluid tight communication between the first medical connector and the second medical connector, wherein the elastomeric sealing member seals against the second medical connector to effect the enhanced contamination prevention between the first and second medical connectors in an intravenous infusion catheter system.

2. The method of claim 1, wherein the elastomeric sealing member is stretched to engage the outer surface of the shroud of the first medical connector.

3. The method of claim 1, wherein the first seal extends between the elastomeric sealing member and the first medical connector along an entire circumference of the outer surface of the shroud.

4. The method of claim 1, wherein the elastomeric sealing member seals an interface between the second medical connector and the first medical connector.

5. The method of claim 1, wherein a portion of the elastomeric sealing member is positioned between the shroud and the second medical connector.

6. The method of claim 1, wherein the elastomeric sealing member extends around the second medical connector.

7. The method of claim 1, wherein the elastomeric sealing member comprises a passageway extending through the elastomeric sealing member, and wherein the passageway is configured to receive at least the portion of the complimentary end.

8. The method of claim 1, wherein the first seal comprises a water-tight seal.

9. The method of claim 1, wherein the complimentary end of the second medical connector comprises a radially extending portion.

10. The method of claim 1, wherein the second medical connector is connected to a tubing.

11. The method of claim 10, wherein the elastomeric sealing member is configured to extend over the second medical connector and to provide a seal with the tubing.

12. The method of claim 1, wherein the elastomeric sealing member is configured to completely enclose the second medical connector.

\* \* \* \* \*